United States Patent
Houser

(10) Patent No.: US 10,363,088 B2
(45) Date of Patent: Jul. 30, 2019

(54) ELECTROSURGICAL TOOL INCLUDING A NON-LINEAR RESISTANCE MATERIAL

(71) Applicant: Ethicon LLC, Guaynabo, PR (US)

(72) Inventor: Kevin L. Houser, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 212 days.

(21) Appl. No.: 15/641,503

(22) Filed: Jul. 5, 2017

(65) Prior Publication Data

US 2019/0008578 A1 Jan. 10, 2019

(51) Int. Cl.
*A61B 18/00* (2006.01)
*A61B 18/12* (2006.01)
*A61B 18/14* (2006.01)

(52) U.S. Cl.
CPC ...... *A61B 18/1442* (2013.01); *A61B 18/1206* (2013.01); *A61B 18/14* (2013.01); *A61B 2018/0072* (2013.01); *A61B 2018/00184* (2013.01); *A61B 2018/00636* (2013.01); *A61B 2018/00666* (2013.01); *A61B 2018/00672* (2013.01); *A61B 2018/00678* (2013.01); *A61B 2018/00696* (2013.01); *A61B 2018/00702* (2013.01); *A61B 2018/00708* (2013.01); *A61B 2018/00767* (2013.01); *A61B 2018/00773* (2013.01); *A61B 2018/00827* (2013.01); *A61B 2018/00875* (2013.01); *A61B 2018/00892* (2013.01)

(58) Field of Classification Search
CPC .......... A61B 2018/00636; A61B 2018/00666; A61B 2018/00672; A61B 2018/00678; A61B 2018/00696; A61B 2018/00702; A61B 2018/00708; A61B 2018/0072; A61B 2018/00767; A61B 2018/00773; A61B 2018/00827; A61B 2018/00875; A61B 2018/00892; A61B 18/1206; A61B 18/14; A61B 18/1442
See application file for complete search history.

(56) References Cited

U.S. PATENT DOCUMENTS

| | | | |
|---|---|---|---|
| 6,978,921 B2 | 12/2005 | Shelton, IV et al. | |
| 8,888,809 B2 | 11/2014 | Davison et al. | |
| 9,585,715 B2 | 3/2017 | Strobl | |
| 2013/0161374 A1 | 6/2013 | Swayze et al. | |

FOREIGN PATENT DOCUMENTS

| WO | WO-2014151621 A1 | 9/2014 |
|---|---|---|
| WO | WO-2014151952 A1 | 9/2014 |

OTHER PUBLICATIONS

U.S. Appl. No. 15/200,283 entitled "Methods, Systems, and Devices for Initializing a Surgical Tool" filed Jul. 1, 2016.
U.S. Appl. No. 15/237,653 entitled "Methods, Systems, and Devices for Controlling a Motor of a Robotic Surgical System" filed Aug. 16, 2016.

*Primary Examiner* — Ronald Hupczey, Jr.
*Assistant Examiner* — Bradford C. Blaise
(74) *Attorney, Agent, or Firm* — Mintz Levin Cohn Ferris Glovsky and Popeo, P.C.

(57) ABSTRACT

Methods, devices, and systems related to electrosurgical tools are provided. The electrosurgical tools can include an electrode formed of non-linear resistance material for allowing energy to be transmitted to the electrode for heating the electrode or to tissue adjacent the electrode for heating the tissue. Such transmission of the energy can depend upon a characteristic of the electrical energy, such as voltage or frequency of the energy, which can affect the resistance properties of the electrode.

19 Claims, 5 Drawing Sheets

ELECTROSURGICAL TOOL INCLUDING A NON-LINEAR RESISTANCE MATERIAL

FIELD

The present disclosure relates generally to electrosurgical tools including a non-linear resistance material.

BACKGROUND

Surgical devices are used in various open, endoscopic, and laparoscopic surgeries to manipulate tissue, staple tissue, and/or transect tissue volumes and blood vessels. These devices can include jaws for grasping tissue therebetween and, in at least some devices, a cutting mechanism that can be advanced through the grasped tissue to transect the tissue. The cutting mechanism can be designed to travel within a track formed in one or both jaws. The devices can also be used to seal tissue volumes and blood vessels being transected, for instance by applying electrical energy to the grasped tissue to seal it before tissue transection is completed. For example, various mono-polar and bi-polar radio frequency (RF) surgical instruments and surgical techniques have been developed for sealing tissue volumes and blood vessels. Electrodes can be disposed on a face of one or both of the jaws and can, for example, apply energy to the grasped tissue.

For surgical devices that include an electrode on at least one jaw, the electrode can be caused to increase in temperature to allow the electrode to treat tissue, such as seal the tissue. After treatment, a user of the surgical device may need to wait for the electrode to cool before moving the electrode or subsequently using the jaws. Such waiting for the electrode to cool can prolong a surgical procedure and increase risk of unintended damage to tissue. Furthermore, some surgical devices that include an electrode on at least one jaw can deliver energy, such as RF, to tissue adjacent the electrode for heating the tissue. However, delivering the energy to tissue for heating can result in non-localized heating of the tissue, which can cause unintended heating of some tissue and possible unwanted damage to such tissue.

Accordingly, there remains a need for improved electrosurgical tools having electrodes.

SUMMARY

In general, methods, devices, and systems related to electrosurgical tools including a non-linear resistance material are provided. In one aspect, a surgical device is provided that in one embodiment includes a housing, an elongate shaft extending distally from the housing, and an end effector at a distal end of the elongate shaft. The end effector can include a pair of jaws configured to grasp tissue therebetween, and the pair of jaws can include at least one electrode formed of a non-linear resistance material. An actuator can be coupled to the housing and configured to be actuated to deliver electrical energy to the at least one electrode upon actuation of the actuator. When the electrical energy is delivered with a voltage below a predetermined threshold voltage, the electrical energy can be transmitted through the tissue grasped by the end effector to heat the tissue. Additionally, when the electrical energy is delivered with the voltage at or above the predetermined threshold voltage, the electrical energy can heat the at least one electrode to heat the tissue.

The surgical device can have any number of variations. For example, a resistance of the at least one electrode can be dependent on at least one of the voltage, a frequency, and a temperature. For yet another example, a resistance of the at least one electrode can be greater when the delivered voltage is at or above the predetermined threshold than when the delivered voltage is below the predetermined threshold. For still another example, the non-linear resistance material can include at least one of silicone carbide, tin oxide, iron oxide, titanium dioxide, and zinc oxide. For another example, the predetermined threshold voltage can be predetermined based on the non-linear resistance material forming the at least one electrode. For still another example, when the electrical energy is delivered with the voltage below the predetermined threshold voltage the electrical energy may not substantially heat the at least one electrode, and when the electrical energy is delivered with the voltage at or above the predetermined threshold voltage the electrical energy may not be substantially transmitted through the tissue grasped by the end effector. For another example, the electrical energy can be radio-frequency energy.

In another embodiment, a surgical device includes an elongate shaft having an end effector at a distal end thereof. The end effector has a tissue engagement surface configured to contact tissue, and the tissue engagement surface has thereon at least one electrode that is configured to contact the tissue and is formed of a non-linear resistance material. The at least one electrode is configured to heat the contacted tissue in a first mode, in which the at least one electrode delivers electrical energy into the contacted tissue to heat the contacted tissue when a voltage is delivered to the at least one electrode on a first side of a predetermined threshold voltage, and in a second mode, in which the at least one electrode is heated to heat the contacted tissue when the voltage is delivered to the at least one electrode on a second side of the predetermined threshold voltage, the second side opposing the first side of the predetermined threshold voltage.

The surgical device can vary in any number of ways. For example, the surgical device can further include at least one electrical lead extending along the elongate shaft that is configured to deliver the voltage to the at least one electrode from a generator. For another example, the surgical device can further include a proximal handle portion having the shaft extending distally therefrom, and the proximal handle portion can include an actuator configured to be actuated in response to a user input thereto, the actuation causing the voltage to be delivered to the at least one electrode. For still another example, the at least one electrode can be configured to automatically switch between the first and second modes. For yet another example, the non-linear resistance material can include at least one of silicone carbide, tin oxide, iron oxide, titanium dioxide, and zinc oxide. For another example, the surgical device can further include a controller associated with the actuator for controlling a voltage of the electrical energy.

In another aspect, a surgical method is provided that in one embodiment includes actuating an actuator to provide electrical energy at a first voltage setting that is on a first side of a predetermined threshold voltage to an electrode at an end effector of a surgical device in contact with tissue, allowing the electrical energy to heat the electrode, actuating the actuator to provide electrical energy at a second voltage setting that is on a second side of the predetermined threshold voltage to tissue positioned adjacent the electrode, and allowing the electrical energy to heat the tissue. Furthermore, the second side can oppose the first side of the predetermined threshold voltage.

The surgical method can vary in any number of ways. For example, the surgical method can further include automatically setting the voltage above or below the predetermined threshold voltage. For another example, the surgical method can further include sensing a temperature of at least one of the electrode and the tissue, and deactivating the actuator when the sensed temperature is above a first threshold value. For still another example, the surgical method can further include deactivating the actuator after the electrical energy has been delivered for a predetermined amount of time. For yet another example, the surgical method can further include controlling a controller associated with the actuator for setting the voltage above or below the predetermined threshold value. For another example, the non-linear resistance material can include at least one of silicone carbide, tin oxide, iron oxide, titanium dioxide, and zinc oxide.

In another embodiment, a surgical method includes receiving, at a processor associated with the surgical device system, a first voltage setting that is within a first voltage range and actuating, based on the received first voltage setting, an actuator to provide electrical energy at the first voltage setting to an electrode at an end effector of a surgical device in contact with tissue thereby causing the electrical energy to heat the electrode. The surgical method further includes receiving, at the processor, a second voltage setting that is within a second voltage range and actuating, based on the received second voltage setting, the actuator to provide electrical energy at the second voltage setting to tissue positioned adjacent the electrode thereby causing the electrical energy to heat the tissue.

BRIEF DESCRIPTION OF DRAWINGS

This invention will be more fully understood from the following detailed description taken in conjunction with the accompanying drawings, in which.

DETAILED DESCRIPTION

Figure 1:
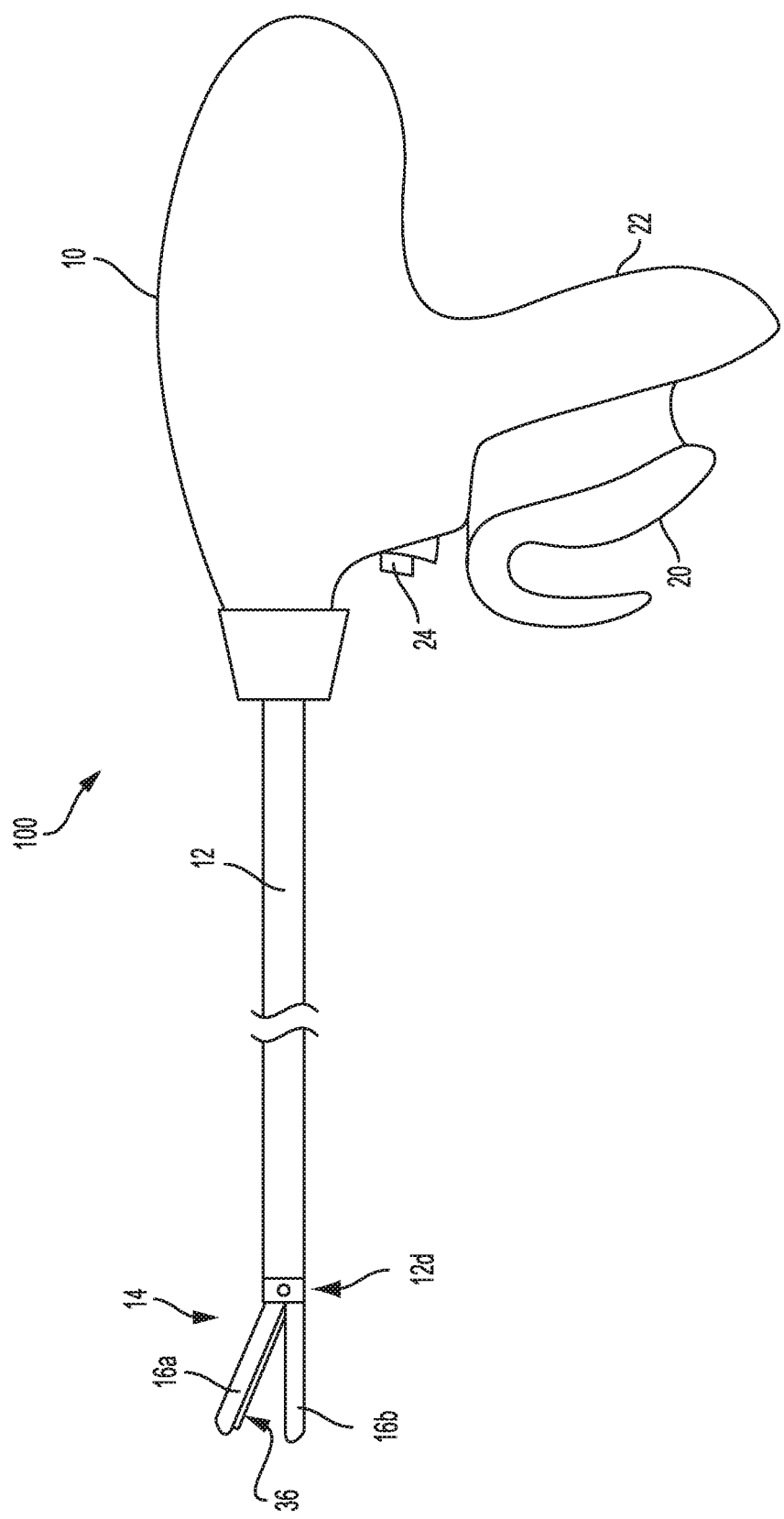
FIG. 1 is a side schematic view of one embodiment of a surgical device.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Methods, devices, and systems for electrosurgical tools including a non-linear resistance material are provided. In general, the electrosurgical tool can be configured to deliver energy to an electrode of the electrosurgical tool or across tissue adjacent the electrode. The energy delivered to the electrode or tissue can include, for example, electrical energy, radio frequency, etc. The non-linear resistance material can form an electrode of the tool and can allow energy to be transmitted to the electrode for heating the electrode or to tissue adjacent the electrode for heating the tissue. Such transmission of the energy can depend upon a characteristic of the energy, such as voltage or frequency of the energy, which can affect the resistance properties of the electrode. When the energy is delivered to the electrode, the electrode can be heated for allowing the electrode to then heat tissue. When the energy is delivered across the tissue, the tissue can be directly heated as a result of the energy being transmitted across the tissue. Such delivery of the energy to the electrode or the tissue can depend on a voltage of the delivered energy. For example, the non-linear resistance material can increase in resistance as the voltage of energy transmitted to the electrode is increased and can decrease in resistance at lower voltages. The non-linear material of the electrode can thus allow the energy to pass through the electrode to the tissue for directly heating the tissue at lower voltages. Additionally, the non-linear material of the electrode can prevent or limit passage of energy through the electrode at higher voltages, thereby heating the electrode. One or more controls associated with the surgical tool can control the voltage of the energy transmitted to the electrode, thereby controlling whether the electrode or tissue is heated as a direct result of energy transmission. This can allow the surgical tool to efficiently and effectively control heating of the electrode and/or tissue, which may prevent unwanted tissue damage and/or shorten procedure time. Furthermore, some surgical procedures can benefit from heating the electrode, such as for localized spot cauterization, versus direct heating of the tissue, such as for sealing tissue.

In an exemplary embodiment, the energy transmitted to the electrode and/or tissue via the surgical device can be transmitted along at least one electrical wire that extends along the elongate shaft from a generator associated with the surgical device. The surgical device can be configured to removably and replaceably connect to the generator, such as via a cable or cord plugged into the generator. The generator can be configured to control a characteristic (e.g., voltage or frequency) of the energy supplied to the electrode of the surgical device. The surgical device can include an analyzer module, which can be associated with either a computer processor or the generator for collecting and analyzing sensed data, such as temperature data associated with the tissue and/or electrode. The processor can be configured to automatically adjust one or more characteristics of the energy, such as to change the resistance of the electrode thereby changing the energy delivery target, e.g., the electrode for heating the electrode or the tissue for heating the tissue.

Figure 2:
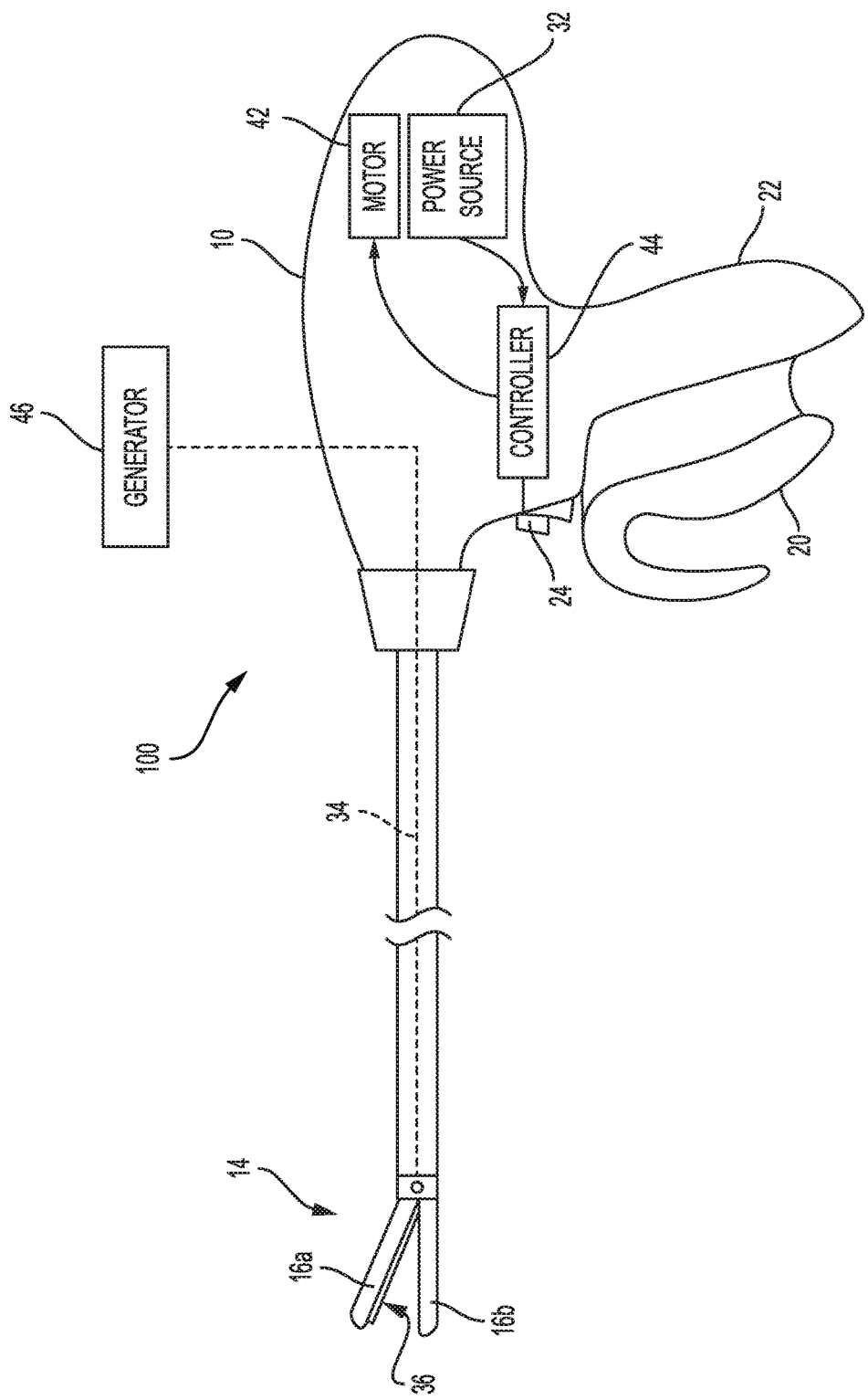
FIG. 2 is a side, partially transparent schematic view of the surgical device of FIG. 1.
Figure 3:
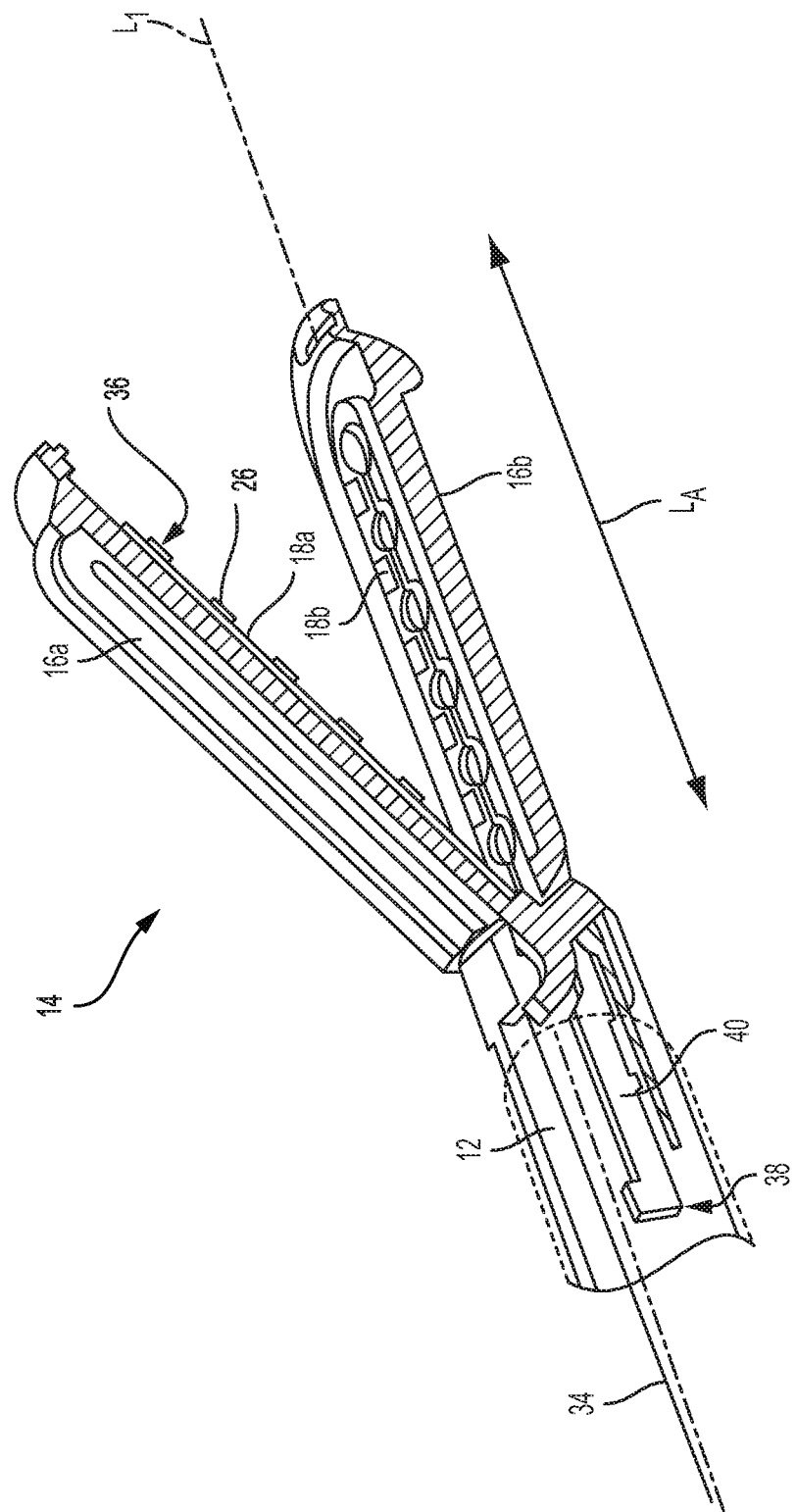
FIG. 3 is a perspective, partially cross-sectional and transparent schematic view of a distal portion of the surgical device of FIG. 1.

FIGS. 1 and 2 illustrate one exemplary embodiment of a surgical device 100 including an elongate shaft 12 having an end effector 14 at a distal end 12d thereof. A distal portion of the device 100 is illustrated in FIG. 3. The shaft 12 extends distally from a housing or proximal handle portion 10 of the surgical device 100. The shaft 12 can be removably and replaceably attached to the housing 10 or components therein in manners that are known to those skilled in the art. In other embodiments, the shaft 12 can be integrally formed with the housing 10.

The housing 10 can be any type of pistol-grip or other type of handle that is configured to carry and/or engage various components used in conjunction with actuating the end effector 14, such as motors, controllers, levers, triggers, sliders, and/or other components, and/or with performing other surgical functions or movements of the device 100. The housing 10 includes a closure actuator 20 and includes a stationary arm 22, also referred to herein as a stationary handle. In general, the closure actuator 20 is configured to be actuated, e.g., moved relative to the stationary arm 22, to control opening and closing of upper and lower jaws 16a, 16b of the end effector 14. A person skilled in the art will appreciate that while the term "handle" can be used in conjunction with the stationary arm 22, in some embodiments, such as those that involve actuation of the closure actuator by a robotic surgical system, electronic system, or other controlled system and thus do not involve manual actuation of the closure actuator, the stationary arm 22 does not have to be "handled" by hand. Thus, the stationary arm 22 can serve as a reference point to describe the location of the closure actuator 20, and does not have to be "handled" by hand. Similarly, the handle portion 10 need not be "handled" by hand.

In some embodiments, the housing 10 can be configured for use with a robotic surgery platform, as opposed to a user's hand. In such embodiments, the closure actuator 20 can have a different configuration than shown in the embodiment of FIGS. 1 and 2, such as by being included as part of a tool housing configured to be operatively coupled to the robotic surgery platform to allow the robotic surgery platform to provide inputs to the tool housing to selectively open and close the end effector 14, e.g., to provide an input to the tool housing to cause linear movement of a rod or other force-translating component of the surgical device, and/or to selectively cause other tool functions, such as energy application. Various embodiments of tool housings of surgical instruments configured to be operatively coupled to a robotic surgery platform are further described in International Pat. Pub. No. WO 2014/151952 entitled "Compact Robotic Wrist" filed Mar. 13, 2014, International Pat. Pub. No. WO 2014/151621 entitled "Hyperdexterous Surgical System" filed Mar. 13, 2014, U.S. patent application Ser. No. 15/200,283 entitled "Methods, Systems, And Devices For Initializing A Surgical Tool" filed Jul. 1, 2016, and in U.S. patent application Ser. No. 15/237,653 entitled "Methods, Systems, And Devices For Controlling A Motor Of A Robotic Surgical System" filed Aug. 16, 2016, which are hereby incorporated by reference in their entireties.

The jaws 16a, 16b can be configured to grasp tissue, and then additional surgical functions can be performed on the grasped tissue using the device 100 and/or other surgical tools, such as cutting or transecting and/or sealing the tissue. While the illustrated end effector 14 has a pair of opposed jaws 16a, 16b, other types, size, shapes, and configurations of end effectors can be used as an end effector in the surgical devices described herein.

The shaft 12 includes a passageway 38 extending longitudinally therethrough along a longitudinal axis $L_1$ of the shaft 12. The passageway 38 is configured to contain therein one or more mechanisms, such as a drive shaft 40 to facilitate end effector 14 opening and closing, one or more electrical leads 34 to facilitate energy delivery, etc.

The end effector 14 includes the first, upper jaw 16a and the second, lower jaw 16b, one or both of which can be configured to move about the longitudinal axis $L_1$ of the shaft 12 to open and close the end effector 14. When the jaws 16a, 16b are in the closed position, opposed tissue-engagement surfaces 18a, 18b of the jaws 16a, 16b can be in direct contact with one another when tissue is not disposed between the jaws 16a, 16b. Alternatively, the tissue engagement surfaces 18a, 18b of the jaws 16a, 16b can be spaced a small distance apart from one another when the jaws 16a, 16b are in the closed position, which may facilitate tissue disposed between the jaws 16a, 16b being adequately held by the jaws 16a, 16b when the jaws 16a, 16b are in the closed position.

The jaws 16a, 16b can each have a substantially elongate and straight shape as in this illustrated embodiment, but one or both of the jaws 16a, 16b can have another shape, such as by being curved relative to the longitudinal axis $L_1$. The jaws 16a, 16b can have any suitable axial length $L_A$ for engaging tissue. The axial length $L_A$ of the jaws 16a, 16b can be selected based on any number of factors, such as the targeted anatomical structure for transection and/or sealing, the size, shape, and configuration of the other components of the device 100, etc.

Either one or both of the jaws' tissue engagement surfaces 18a, 18b can include one or more surface features thereon that are configured to help secure tissue grasped between the jaws 16a, 16b. For example, the one or more surface features can include a friction feature, such as teeth, ridges, or depressions, configured to increase friction between the grasped tissue and the surfaces 18a, 18b of the jaws 16a, 16b without tearing or otherwise damaging the tissue in contact with the one or more surface features. The one or more surface features can also be configured to facilitate the grasping tissue and forming substantially smooth, uniform layers of tissue to improve tissue effect. In this illustrated embodiment, one or more surface features in the form of a plurality of teeth 26 are positioned along an axial length of both of the engagement surfaces 18a, 18b. The first and second jaws 16a, 16b can include features for interacting with a force-translating component, such a compression member, rod, or other structure extending through the shaft 12 and configured to effect at least one function of the end effector 14 such as closing, cutting tissue, etc.

As shown in FIG. 3, the end effector 14 of the surgical device 100 can include an electrode 36 on at least one of the first and second jaws, 16a, 16b. Only the upper jaw 16a includes at least one electrode 36 in this illustrated embodiment, e.g., the electrode 36 on the upper jaw tissue engagement surface 18a, but in other embodiments only the lower jaw 16b can include at least one electrode or each of the upper and lower jaws 16a, 16b can include at least one electrode. For example, the electrode 36 can form an entire tissue engagement surface 18a, 18b of either jaw 16a, 16b, or the electrode 36 can form only a part of the tissue engagement surface 18a, 18b of either jaw 16a, 16b. In at least some implementations, the electrode 36 can be positioned at a distal end of either jaw 16a, 16b, which can, for example, be beneficial for performing spot cauterization of tissue.

The electrode 36 can have a variety of sizes, shapes, and configurations. For example, the electrode 36 can be substantially flat and complementary to the substantially flat tissue-engagement surfaces 18a, 18b of the respective upper and/or lower jaw 16a, 16b. Energy can be supplied to the electrode 36, for instance by the firing actuator 24, as described in greater detail below.

The electrode 36 can be formed of a non-linear resistance material such that the resistance of the electrode 36 can be configured to change based on at least one property associated with the surgical device 100 and/or tissue adjacent the end effector 14 of the surgical device 100. For example, the resistance of the electrode 36 can change based on a voltage of the energy being transmitted to the electrode 36. As discussed further below, the non-linear resistance material can define a predetermined threshold voltage such that energy having a voltage below the threshold voltage can transmit through the electrode 36, such as transmit through the electrode 36 and through tissue adjacent the electrode 36. This can allow the tissue to be heated as a result of the energy being transmitted through the tissue, such as for sealing tissue. Energy having a voltage that is at or above the threshold voltage can be prevented from transmitting through the electrode 36 and, instead, cause the electrode 36 to increase in temperature. This temperature increase can allow the electrode 36 to be used to cauterize tissue, such as for performing spot cauterization of the tissue. The non-linear resistance material defines the predetermined threshold voltage, thus allowing the electrode 36 to dynamically perform in one of two modes automatically in response to the value of the voltage applied thereto, one mode when the voltage delivered thereto is below the predetermined threshold voltage, and another mode when the voltage delivered thereto is at or above the predetermined threshold voltage.

By changing the voltage of the energy being provided to the electrode 36, the surgical device 100 can switch from transmitting energy to the electrode 36 (e.g., for heating the electrode 36) to transmitting the energy through the tissue (e.g., for heating the tissue). In some instances, it can be beneficial to heat the electrode 36, such as for performing cauterization, including spot cauterization. However, it may be more efficient and effective in other instances to directly heat the tissue, such as for tissue sealing, and not cause the electrode 36 to become heated. For example, allowing the energy to be transmitted through the tissue can result in non-localized heating of tissue, which can be effective for tissue sealing but ineffective for spot cauterization. However, allowing the electrode 36 (instead of the tissue) to become heated can allow for more localized heating of tissue by applying the heated electrode 36 to specific areas of the tissue (e.g., spot cauterization). The ability to use the surgical device 100 for tissue sealing without heating the electrode 36 may prevent having to wait until the electrode 36 cools before being able to move or subsequently use the end effector 14 without causing unwanted tissue damage.

As mentioned above, the electrode 36 can be formed of one or more non-linear resistance materials. In general, a non-linear resistance material has a non-linear relationship between voltage and current such that as voltage is applied across the resistor, the current flowing across the resistor increases and the resistance decreases. Once a voltage equal to or greater than a predetermined threshold voltage is applied, the resistance decreases significantly, and the corresponding current increases significantly so as to define the non-linear nature of the material. Non limiting examples of non-linear resistance materials include silicone carbine (SiC), tin oxide ($SnO_2$), iron oxide ($Fe_2O_5$), titanium dioxide mixed with very small or trace amounts of bismuth oxide and an oxide of a semi-conductive element, and zinc oxide (ZnO), although other non-linear resistance materials may be used.

The resistance of the non-linear resistance material(s) forming the electrode 36 can depend upon one or more properties, such as the voltage or frequency of the energy transmitted to the electrode 36 and/or the temperature of either the electrode 36 or tissue adjacent the electrode 36.

Figure 4:
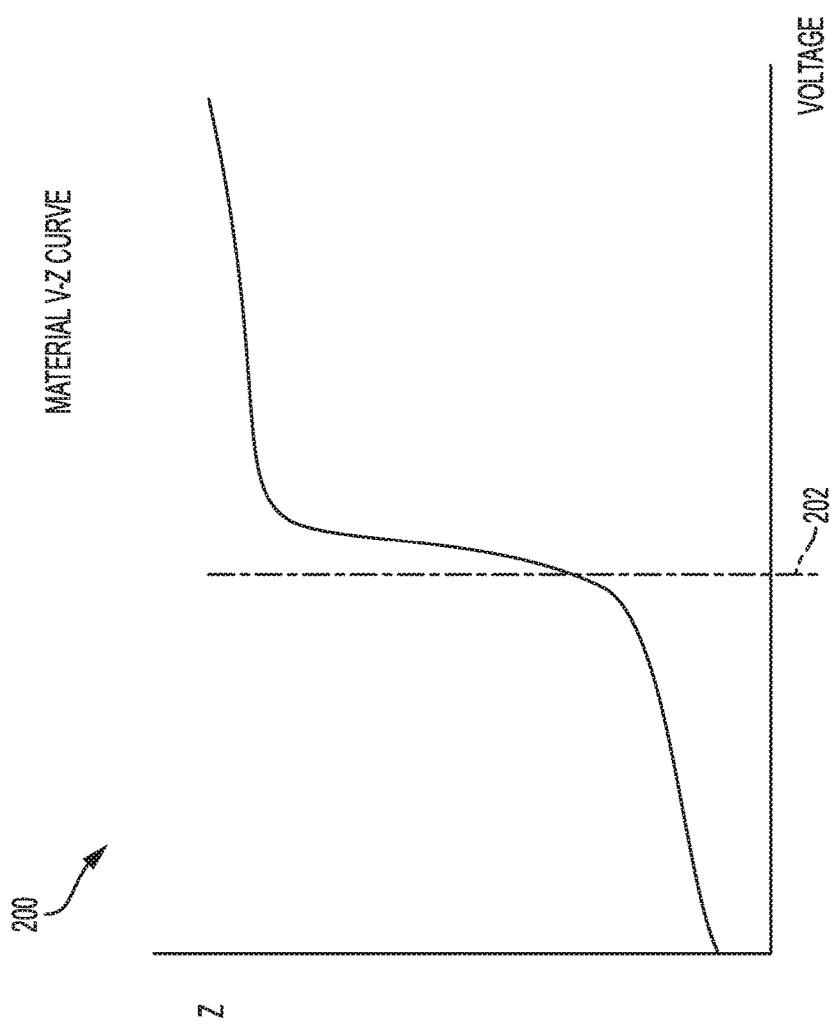
FIG. 4 is a graph illustrating voltage versus resistance properties of a non-linear material forming an electrode.

FIG. 4 illustrates a graph 200 showing resistance (z) of the non-linear resistance material of the electrode 36 as a function of voltage. As shown in FIG. 4, at lower voltages (e.g., below a threshold voltage 202), the resistance is lower and at higher voltages (e.g., at or above the threshold voltage 202) the resistance is higher. As such, energy transmitted at the lower voltages to the electrode 36 formed of the non-linear resistance material can transmit across tissue adjacent the electrode 36, thereby heating the tissue. Furthermore, energy transmitted at the higher voltages to the electrode 36 can be prevented from transmitting across tissue and, instead, can cause the electrode 36 to increase in temperature. As discussed above, the threshold voltage 202 can be predetermined based on the type of non-linear resistance material forming the electrode 36. Furthermore, although the graph 200 shows the resistance being low when the voltage is low and the resistance as being high when the voltage is high, various other non-linear relationships between the voltage and resistance of the electrode 36 can exist. For example, the resistance can be low when the voltage is high and the resistance can be high when the voltage is low.

As shown in FIGS. 1-2, the surgical device 100 includes a firing actuator 24 configured to deliver energy to the electrode 36 for heating the electrode 36 or across tissue for heating the tissue. Actuation of the firing actuator 24 is configured to allow electrical energy to pass through the one or more electrical leads 34 that extend through the shaft 12 to the at least one electrode 36 located at the end effector 14. A power source 32 can be disposed in the housing 10, as in this illustrated embodiment, or the power source 32 can be external of the housing 10. The housing 10 can be configured to electrically connect to an external power source, such as by way of a socket extending from the housing 10 to connect to the power source, e.g., by using a cord extending from the housing 10 or by using another connection. The firing actuator 24 in this illustrated embodiment is in the form of a button but can have other configurations, e.g., a lever, a knob, etc. The firing actuator 24 can be configured to effect a function of the end effector 14 in addition to or instead of applying energy.

The device 100 can include a motor 42 and a controller 44 each disposed within the housing 10, as in this illustrated embodiment. Activation of the motor 42, e.g., by actuating the closure actuator 20, can be configured to close the jaws 16a, 16b. The controller 44 can be configured to operatively couple the firing actuator 24 and the power source 32 such that actuation of the firing actuator 24 causes energy application. The motor 42, power source 32, and controller 44 can be disposed at various locations in the device 100, such as in the proximal handle portion 10, although any one or more of the motor 42, power source 32, and controller 44 can be located off-board of the device 100 and operatively coupled thereto, such as with a cord or other wired or wireless connection. In other embodiments, the surgical device can lack the motor, power source, and controller such that end effector opening/closing and compression member advancement/retraction can be manually accomplished.

Exemplary embodiments of devices and methods for grasping and sealing tissue are further described in U.S. Pat. No. 9,585,715 entitled "Electrosurgical Sealing And Transecting Devices And Methods With Improved Application Of Compressive Force" filed Jan. 7, 2014, U.S. Pat. Pub. No. 2013/0161374 entitled "Layer Arrangements For Surgical Staple Cartridges" filed Feb. 8, 2013, U.S. Pat. No. 8,888,809 entitled "Surgical Instrument With Jaw Member" filed Oct. 1, 2010, and U.S. Pat. No. 6,978,921 entitled "Surgical Stapling Instrument Incorporating An E-Beam Firing Mechanism" filed May 20, 2003, which are incorporated by reference herein in their entireties.

Figure 5:
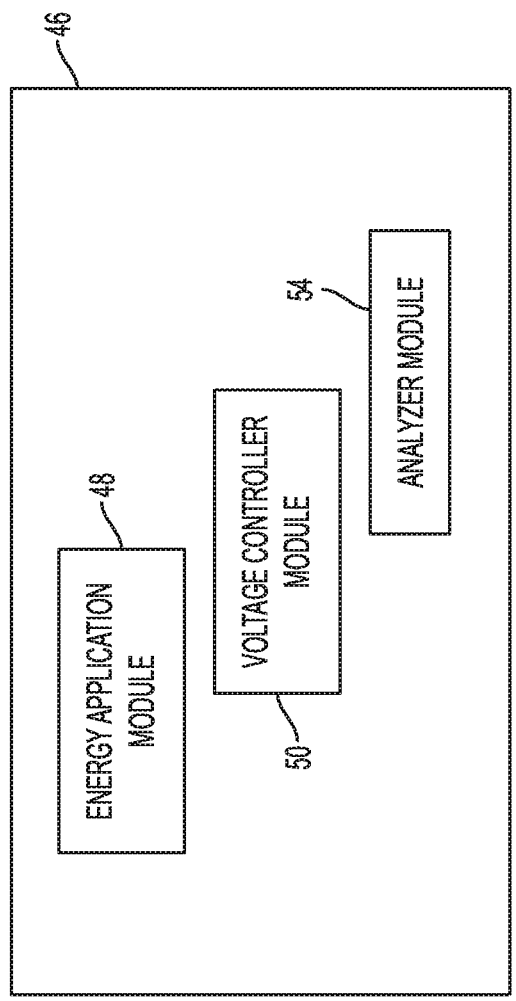
FIG. 5 is a schematic view of a generator of the surgical device of FIG. 1.

The device 100 can be configured to operatively connect to a generator 46, shown in FIGS. 2 and 5, to provide an off-board power source for powering one or more components of the device 100, such as delivering energy to the electrode 36 or tissue as an alternate or in addition to the on-board power source 32. The generator 46 can be configured to operatively couple to the firing actuator 24. The generator 46 can have a variety of configurations, such as a radiofrequency (RF) generator. The generator 46 can be a separate unit from the device 100 that is configured to electrically connect to the device 100, thereby allowing a weight and size profile of the device 100 to be reduced and may allow different types of generators to be operatively coupled to the device 100, e.g., to allow users to select an appropriate generator for a particular procedure, may facilitate repair and/or upgrade of generators, and/or may reduce overall cost of the device 100. The generator 46 can include at least one port configured to physically connect to the surgical device 100 or other surgical device, such as by a cord of the surgical device plugging into the port.

As illustrated in FIG. 5, the generator 46 can include an energy application module 48, a voltage controller module 50, and an analyzer module 54. The modules 48, 50, 54 can each be part of a computer system associated with the generator 46. The computer system can include one or more processors which can control the operation of the computer system and generator. The processor(s) can include any type of microprocessor or central processing unit (CPU), including programmable general-purpose or special-purpose microprocessors and/or any one of a variety of proprietary or commercially available single or multi-processor systems. The computer system can also include one or more memories, which can provide temporary storage for code to be executed by the processor(s) or for data acquired from one or more users, storage devices, and/or databases. The memory can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies. The various elements of the computer system can be coupled to a bus system. The computer system can also include one or more network interface(s), one or more input/output (TO) interface(s), and one or more storage device(s). A computer system can also include any of a variety of other software and/or hardware components, including by way of non-limiting example, operating systems and database management systems. Although an exemplary computer system is described herein, it will be appreciated that this is for sake of generality and convenience. In other embodiments, the computer system may differ in architecture and operation from that shown and described here.

The energy application module 48 can be configured to deliver energy to the surgical device 100 connected thereto to allow energy to transmit to the one or more electrodes 36 for heating the electrodes 36 or transmit across tissue adjacent the electrodes 36 to heat the tissue, as discussed above. The energy application module 48 can thus be configured to operatively couple to the lead(s) 34 of the surgical device 100 such that the lead(s) 34 carry energy supplied by the generator 46 to the electrode(s) 36 and/or tissue.

The voltage controller module 50 can be configured to control the voltage of the energy being transmitted to the surgical device 100 connected thereto. The voltage controller module 50 can be configured to set a low voltage (e.g., below a predetermined threshold voltage) to cause the electrode 36 to have a low resistance, thereby allowing the energy to transmit across tissue for heating the tissue. The voltage controller module 50 can be configured to set a high voltage (e.g., at or above a predetermined threshold voltage) to cause the electrode 36 to have a high resistance, thereby preventing the energy from transmitting across tissue and, instead, heat the electrode 36. The voltage controller module 50 can be configured to be controlled by a user or can be controlled by the computer system. For example, the voltage controller module 50 can be controlled by the computer system, such as for allowing the voltage to be automatically changed (e.g., switched from high to low voltage and vice versa) after determination of one or more parameters. Such parameters can include an amount of time the energy has been applied, a sensed temperature of either the electrode 36 or tissue, etc. Although the voltage controller module 50 is described herein as controlling the voltage of the energy being transmitted, the voltage controller module 50 can be configured to control other characteristics of the energy, such as the frequency of the energy.

The analyzer module 54 can be configured to analyze one or more parameters and/or characteristics for determining an appropriate characteristic (e.g., voltage or frequency) of the energy. In at least some implementations, one or more sensors (e.g., temperature sensor) can be associated with the surgical device 100 for sensing the one or more parameters (e.g., temperature of the tissue and/or electrode 36). The analyzer module 54 can be configured to collect and analyze the sensed parameters for determining appropriate instructions to send to the energy application module 48 and/or the voltage controller module 50. Such instructions can include stopping the transmission of energy to the surgical device 100, and altering a characteristic of the energy (e.g., increase or decrease the voltage or frequency). In at least some implementations, the processor or analyzer module 54 can be configured to stop delivery of the energy after a predetermined duration of energy delivery.

In use, the device 100 can be connected to the generator 46, such as by removably and replaceably coupling the device 100 to the generator 46 by plugging a cord of the device 100 into a port of the generator 46. In other embodiments, as mentioned above, the device 100 can connect to the generator 46 in other ways, or the generator 46 can be on board the device 100. With the device 100 connected to the generator 46, the firing actuator 24 can be actuated to cause heating of the electrode 36 or tissue by setting the voltage or frequency (e.g., via the voltage controller module 50) of the energy being transmitted from the generator 46. In response to actuation of the firing actuator 24, the energy at the set voltage or frequency can be transmitted to the electrode 36 via the lead(s) 34 for heating the electrode 36 or across tissue for heating the tissue depending upon the set voltage or frequency, as described above. For example, after either a predetermined amount of time delivering the energy or once the analyzer module 54 determines a parameter threshold (e.g., temperature of the electrode 36 or tissue) has been exceeded, the controller module 50 can be configured to automatically change a characteristic of the energy (e.g., voltage or frequency) or stop the delivery of energy. The user can also manipulate energy characteristics at any given time by providing input to the generator 46.

A person skilled in the art will appreciate that the devices, systems, and methods disclosed herein have application in conventional minimally-invasive and open surgical instrumentation as well application in robotic-assisted surgery. In some embodiments, the devices, systems, and methods described herein are provided for open surgical procedures, and in other embodiments, the devices, systems, and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods, systems, and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a housing;
an elongate shaft extending distally from the housing;
an end effector at a distal end of the elongate shaft, the end effector including a pair of jaws configured to grasp tissue therebetween, the pair of jaws including at least one electrode formed of a non-linear resistance material;
an actuator coupled to the housing and configured to be actuated to deliver electrical energy to the at least one electrode upon actuation of the actuator;
wherein when the electrical energy is delivered with a voltage below a predetermined threshold voltage the electrical energy is transmitted through the tissue grasped by the end effector to heat the tissue, and when the electrical energy is delivered with the voltage at or above the predetermined threshold voltage the electrical energy heats the at least one electrode to heat the tissue.

2. The surgical device of claim 1, in the electrical energy is radio-frequency energy.

3. The surgical device of claim 1, wherein a resistance of the at least one electrode is dependent on at least one of the voltage, a frequency, and a temperature.

4. The surgical device of claim 1, wherein a resistance of the at least one electrode is greater when the delivered voltage is above the predetermined threshold than when the delivered voltage is below the predetermined threshold.

5. The surgical device of claim 1, wherein the non-linear resistance material includes at least one of a silicone carbide, tin oxide, iron oxide, titanium dioxide, and zinc oxide.

6. The surgical device of claim 1, wherein the predetermined threshold voltage is predetermined based on the non-linear resistance material forming the at least one electrode.

7. The surgical device of claim 1, wherein when the electrical energy is delivered with the voltage below the predetermined threshold voltage the electrical energy does not substantially heat the at least one electrode, and when the electrical energy is delivered with the voltage at or above the predetermined threshold voltage the electrical energy is not substantially transmitted through the tissue grasped by the end effector.

8. A surgical device, comprising:
an elongate shaft having an end effector at a distal end thereof, the end effector having a tissue engagement surface configured to contact tissue, the tissue engagement surface having thereon at least one electrode that is configured to contact the tissue and is formed of a non-linear resistance material, the at least one electrode being configured to heat the contacted tissue in a first mode, in which the at least one electrode delivers electrical energy into the contacted tissue to heat the contacted tissue when a voltage is delivered to the at least one electrode on a first side of a predetermined threshold voltage, and in a second mode, in which the at least one electrode is heated to heat the contacted tissue when the voltage is delivered to the at least one electrode on a second side of the predetermined threshold voltage, the second side opposing the first side of the predetermined threshold voltage.

9. The surgical device of claim 8, further comprising at least one electrical lead extending along the elongate shaft that is configured to deliver the voltage to the at least one electrode from a generator.

10. The surgical device of claim 8, further comprising a proximal handle portion having the elongate shaft extending distally therefrom, the proximal handle portion including an actuator configured to be actuated in response to a user input thereto, the actuation causing the voltage to be delivered to the at least one electrode.

11. The surgical device of claim 8, wherein the at least one electrode is configured to automatically switch between the first and second triodes.

12. The surgical device of claim 8, wherein the non-linear resistance material includes at least one of a silicone carbide, tin oxide, iron oxide, titanium dioxide, and zinc oxide.

13. The surgical device of claim 8, further comprising a controller associated with the actuator for controlling the voltage.

14. A surgical method, the method comprising:
actuating an actuator to provide electrical energy at a first voltage setting that is on a first side of a predetermined threshold voltage to an electrode at an end effector of a surgical device in contact with tissue, the electrode formed of a non-linear resistance material;
allowing the electrical energy to heat the electrode;
actuating the actuator to provide electrical energy at a second voltage setting that is on a second side of the predetermined threshold voltage to tissue positioned adjacent the electrode, the second side opposing the first side of the predetermined threshold voltage; and
allowing the electrical energy to heat the tissue.

15. The method of claim 14, further comprising automatically setting the voltage on the first side or on the second side of the predetermined threshold voltage.

16. The method of claim 14, further comprising sensing a temperature of at least one of the electrode and the tissue, and deactivating the actuator when the sensed temperature is above a first threshold value.

17. The method of claim 14, further comprising deactivating the actuator after the electrical energy has been delivered for a predetermined amount of time.

18. The method of claim 14, further comprising controlling a controller associated with the actuator for setting the voltage above or below the predetermined threshold value.

19. The method of claim 14, wherein the non-linear resistance material includes at least one of a silicone carbide, tin oxide, iron oxide, titanium dioxide, and zinc oxide.

* * * * *